United States Patent [19]

Park et al.

[11] Patent Number: 5,210,292

[45] Date of Patent: May 11, 1993

[54] PROCESS FOR PREPARING POLYMER GRADE TEREPHTHALIC ACID

[75] Inventors: Sang F. Park; Tae S. Chang; Young K. Lee, all of Taejeon; Kyu W. Choi, Seoul, all of Rep. of Korea

[73] Assignee: Korea Research Institute of Chemical Technology, Taejeon, Rep. of Korea

[21] Appl. No.: 596,914

[22] Filed: Oct. 12, 1990

[30] Foreign Application Priority Data

Oct. 13, 1989 [KR] Rep. of Korea .................. 89-14689

[51] Int. Cl.$^5$ .......................................... C07C 51/487
[52] U.S. Cl. .................................. 562/487; 562/480; 562/485
[58] Field of Search ................................ 562/485, 487

[56] References Cited

U.S. PATENT DOCUMENTS 4,716,245 12/1987 Hirose ................................. 562/416
4,820,868 4/1989 Mitamura et al. .................. 562/482

Primary Examiner—José G. Dees
Assistant Examiner—Vera C. Clarke
Attorney, Agent, or Firm—Cushman, Darby & Cushman

[57] ABSTRACT

A process for purifying a crude terephthalic acid obtained by neutralization of the disodium terephthalate from alkali waste water from a polyester fabric-treatment process, into polymer grade terephthalic acid. The crude terephthalic acid is crushed, and fed to the kiln at 150°–300° C. for thermal treatment in an aqueous solution. The ammoniated, and the impurities in the solution are removed by adsorption followed by deammoniation, which may be accomplished by heating or by treatment with sulfuric acid.

5 Claims, 1 Drawing Sheet

PROCESS FOR PREPARING POLYMER GRADE TEREPHTHALIC ACID

BACKGROUND OF THE INVENTION

This invention relates to a process for preparing polymer grade terephthalic acid from the disodium terephthalate contained in waste water from weight-reduction process in a polyester textile dyeing complex.

In general, in the prior art, disodium terephthalate contained in alkali waste water was discharged in a weight reduction-processing stage which is designed to give the polyester textile. A silky property, as well as to improve the dyeing capability by treating the polyester textile with sodium hydroxide or another basic aqueous solution at high temperature, and thereby causing a part of the textile to become depolymerized.

That alkali treatment technology for a polyester textile, causes the formation of the disodium terephthalate waste water. That alkali treatment technology was developed by Imperial Chemical Industries(England) in 1952, and it was well known that the weight of polyester could be reduced 15%-30% by treating the polyester textile with a sodium hydroxide solution. [M. N. Chapatwala, "Weight Reduction of Polyester" Colourage Dec. 1986].

Korea is one of the leading textile production countries in the world. Accordingly, in the past, a considerable amount of sodium terephthalate contained in waste water has been discharged because a large amount of polyester textile is treated by weight reduction process and this waste water that has been generated as a result, has been treated by a conventional method without a recovery of terephthalic acid from the waste water.

Therefore, instead of simply giving good properties to the polyester textile practicing the conventional weight reduction process not only has caused a loss of terephthalic acid, but also has caused severe environmental problems, when the disodium terephthalate contained in alkali waste water has been discharged directly into the environment.

Accordingly, the recovery of terephthalic acid from alkali waste water shows great concern, both as to reutilization of terephthalic acid and the reduction of the load in treating, waste water.

The conventional weight-reduction process for polyester textile includes treating the polyester textile on about 2-12% sodium hydroxide solution at 60° C.-130° C. for a specified time. By using such a process, one can provide the polyester textile with a desirable property in which the surface of polyester textile is partly decomposed.

If the polyester textile, is treated with sodium hydroxide solution to reduce weight, a large amount of hydrophilic group is formed on the surface of the textile and some physical properties of the textile, such as the flexibility, absorption property, anti-electrification property, anti-contamination property, and so on, can be enhanced. By using the prior art method this changes in the physical properties exhibits similar touch and function to those of the natural fiber, silk.

In the course of conducting the alkali weight reduction process, disodium terephthalate and ethylene glycol are formed by depolymerization of the polyester on the surface of textile mixed with water for alkali waste water. This waste water should be treated to prevent pollution, but such treatment conventionally requires a large amount of investment for anti-pollution facilities or acids, such as the sulfuric acid which is used for neutralization of the waste water.

Recently, various methods relating to the recovery of terephthalic acid from the disodium terephthalate contained in water and on purifying crude terephthalic acid are reported. These related technologies are as follows:

In Japanese Patent Laid Open Publication No. 56-40,640, Crude terephthalic acid (16.6 parts) was dissolved in 2N-NaOH(150 parts), and 5% active chlorine contained NaOCl solution (8.25 parts) and 3.5% $H_2O_2$ were added thereto, and the resulting solution was stirred for 60 minutes at 80° C. to get the terephthalic acid having 90% of transmittance at 340 nm.

In Japanese Patent Laid Open Publication No. 46-19,619, crude terephthalic acid was dissolved in aqueous ammonia solution to recrystallize as ammonium salt and the resulting ammonium salt was treated with $KMnO_4$ followed by passing the resulting aqueous solution through active charcoal, to thereby obtain a quantity of purified terephthalic acid.

In Japanese Patent Laid Open Publication No. 56-83,443, a solution containing terephthalic acid (150 parts) was washed with 2N-NaOH solution (1000 parts) having and water (150 parts), added $KMnO_4$ (12 parts), reacted for 2 hrs at 80° C. and treated with powdered active charcoal for 2 hrs at 80° C. to thereby obtain terephthalic acid having 32% of transmittance. The above product was treated with 10% acetic acid solution (100 parts) for 1.5 hrs at 230° C., and yielded terephthalic acid having 93% transmittance. (If the sample was not treated with $KMnO_4$, the transmittance was 1%).

In Japanese Patent Laid Open Publication No. 56-113,738, crude terephthalic acid (150 parts) was dissolved in 2N-KOH (15 parts), water (500 parts) added thereto, and the reaction solution was stirred for 2 hrs at 250° C., under a pressure of 20 atm. The resulting solution was cooled, $KMnO_4$ (4.5 parts) was added thereto, at 90° C., and reacted for 2 hrs. The solution was filtered to remove $MnO_2$ and precipitated with sulfuric acid, and yielded terephthalic acid having 16% transmittance. The recovered terephthalic acid was treated with acetic acid-water (9:1) solution (100 parts) for 1.5 hrs at 230° C. cooled, and filtered to thereby provide terephthalic acid having 92% transmittance.

In Japanese Patent Laid Open Publication No. 56-103,136, crude terephthalic acid (5.56 g) was hydrogenated in the presence of active charcoal 2%(1% ruthenium content) and active charcoal (1.0 wt % carbon) to obtain terephthalic acid having 62.9% transmittance.

In French Patent No. 1,592,084, crude terephthalic acid was dissolved in NaOH solution, and the pH of the solution was controlled to 9.0. That pH-controlled solution was heated to 50° C.-60° C. and sodium chloride was added thereto. After 30 min., the solution was filtered, and sulfuric acid was added to it in order to obtain terephthalic acid.

In Japanese Patent Laid Open Publication No. 45-11,293, crude terephthalic acid was dissolved in ammonia water, oxidized with $KMnO_4$, and 8-hydroquinone was added thereto. The resulting solution was extracted with hydrochloric acid to obtain terephthalic acid.

In U.S. Pat. No. 3,849,489, crude terephthalic acid was dissolved in ammonia water, and heated to 290° C. to recover terephthalic acid. The recovered terephthalic acid was dissolved again in ammonia water, and oxidized with $MnO_2$. After 30 min., the solution was filtered, passed through active charcoal heated to 290° C. for deammoniation, and terephthalic acid thereby obtained.

According to the reported methods, the crude terephthalic acid was purified by dissolving or washing with alkali solution such as NaOH or KOH, by treating at high temperature and high pressure using active charcoal for adsorption, or by treating with oxidizing agents or reducing agents such as $MnO_2$, $KMnO_4$ or hydrogen gas. The alkali transmittance was measured to identify the purity of the finally obtained terephthalic acid, but the values were always less than 93%.

These reported methods have also several problems, i.e., they are economically unfavorable because they use chemicals as oxidizing agents, and it requires long time to complete the processes.

In addition, the purity was identified only by alkali transmittance, and there can be come problems in testing the other physical properties.

Besides the above problems, terephthalic acid which can be reused in the polymerization reactions, should have more than 95% of alkali transmittance, so the terephthalic acid obtained by the reported methods was not sufficient to use as a polymer grade terephthalic acid.

Especially, it was regarded as a very difficult technology to get the sufficiently purified terephthalic acid as for the polymer grade, which can be reused in the polymerization reactions, from the recovered waste water, and the solution of this problem has importance not only in regard to the treatment of waste water for abating the environmental problem but also the recycling benefit of permitting utilization of terephthalic acid as a polymer grade.

SUMMARY OF THE INVENTION

Therefore, the object of present invention is to provide a process for preparing a polymer grade terephthalic acid from alkali waste water in which disodium terephthalate is contained with impurities.

This invention relates to a process for purifying a crude terephthalic acid obtained by neutralization of the disodium terephthalate from alkali waste water, so as to provide polymer grade terephthalic acid. In practicing this method, the crude terephthalic acid is crushed, fed to the kiln at 150°-300° C. for thermal treatment, and then ammoniated. The impurities in the solution state are removed by adsorption followed by deammoniation.

DETAILED DESCRIPTION OF THE PRESENTLY PREFERRED EMBODIMENTS

Figure 1:
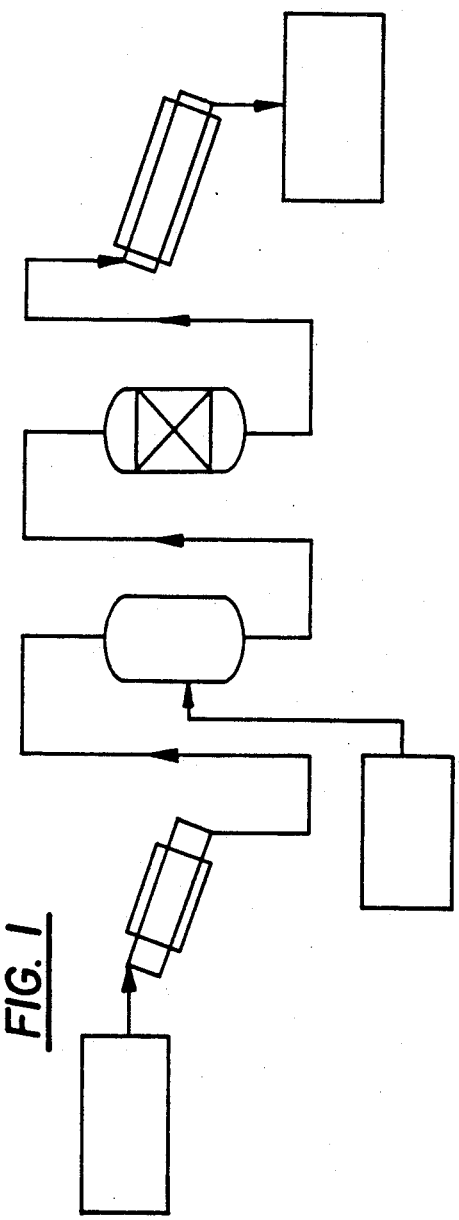
FIG. 1 is a flow chart of a first embodiment of the process of the invention, in which diammonium terephthalate is deammoniated, by heating to more than 200° C., in order to obtain polymer-grade terephthalic acid.

According to this invention, alkali waste water is neutralized first by acid, and washed to obtain crude terephthalic acid. By this washing, mainly salt formed during neutralization is eliminated, with a certain limit. In order to purify the crude terephthalic acid to a sufficient extent, such that it can be used in the polymerization reactions, the crude terephthalic acid is crushed into small particles, and it is treated at 150°-300° C. for the oxidation of impurities contained in the terephthalic acid ("TPA") crude, and this thermally treated crude TPA is ammoniated to obtain a solution phase. The impurities contained ammoniated TPA solution are removed by adsorption in the solution phase with active carbon, and ammonium terephthalate is deammoniated with the acid (FIG. 2), or by thermal treatment (FIG. 1), in order to obtain polymer grade terephthalic acid.

A sodium form of alkali waste water was used as samples for practicing the method of the present invention. These samples were delivered from the textile treating complex at Taegu in Korea. A filter cake of crude TPA was obtained by neutralizing the sodium form of waste water with sulfuric acid. The resulting filter cake was washed with deionized water until the electric conductivity of the filtrate became 40 $\mu$mhos/cm, and yielded crude terephthalic acid having an acid number of 673-7 KOH mg/, 150 ppm of ash content, 87.8% and 97.0% of alkali transmittance at 340 nm and 400 nm, respectively, less than 1% of thermal resistance, 17 ppm of iron content, 20(APHA) of color, and less than 25 ppm of 4-carboxybenzaldehyde (4-CBA). (Refer to Table 1).

This crude terephthalic acid was suitable in the items of acid number alkali transmittance, 4-CBA, and color for the polymer synthetic standard, but there were difficulties if one attempted to use the crude terephthalic acid in polymer reactions directly, because the ash content, thermal resistance, and iron content were off the specification.

Here, the crude terephthalic acid was prepared from the recovered terephthalic acid, which was obtained by neutralization, by repeated suspension, stirring, filtering, and washing with deionized water.

In practicing an embodiment of the present invention, the recovered terephthalic acid is treated with heat under a stream of oxygen-containing gas to yield a polymer grade terephthalic acid, which has a specification of less than 100 ppm of ash content, more than 90% of thermal resistance, and less than 10 ppm of iron content. This thermal treatment exposes the impurities which could not otherwise be removed by washing the surface of the filter cake. The impurities exposed in the TPA are transformed into ammoniun form by ammoniation with ammonia in water. This ammoniated solution displays a dark brown color, due to the presence of impurities.

The colored impurities in the ammonium solution are removed by an adsorption process using active carbon, and the purified terephthalic acid is generated by deammoniation by thermal treatment, or by neutralization by acid.

This invention has striking features in the preparation of polymer grade terephthalic acid by thermal treatment before the ammoniation step, i.e., the crude terephthalic acid is crushed, and treated at 150°-300° C. for the impurities to be oxidized, decomposed, and diffused out onto the surface, then ammoniated, and the impurities are removed by adsorption processes.

The impurity-containing terephthalic acid is crashed in to 0.1 to 1.500 $\mu$m, and preferably to 1-100 $\mu$m size to maximize the contacting effect and treated with heat at 150°-300° C. in a rotary kiln under a stream of oxygen-containing gas having an oxygen content of 10 to 100%. As a result, alkali metals such as Ca, Mg, Si, Al, inorganic materials, and colored organic impurities are oxidized, decomposed, and exposed onto the surfaces of the crushed particles.

This process is designed to remove the impurities in the terephthalic acid, and volatile impurities can easily be removed by this thermal treatment process.

Thermal treatment can be performed at 150°–300° C., more preferably at 200°–290° C., for 1 min., to 10 hrs., more preferably for 2 min. to 1 hrs. under the stream of 0.01–1,000 ml/min. of gases.

The preferred oxygen-containing gas is air, with a flow rate and other conditions as indicated in and other conditions as indicated in Table 1.

TABLE 1

| | Condition |
|---|---|
| Gas | |
| flow (LPM) | 0.8 |
| O$_2$ content (%) | 30 |
| Thermal treatment | |
| Time (min) | 10 |
| Rate (rpm) | 1.1–1.5 |
| Temperature (°C.) | 280 |

These thermally treated crushed crude terephthalic crystals are reacted with ammonia and water to make a corresponding ammonium salt solution. In this process, inorganic metals in the impurities are precipitated as insoluble sludges and can easily be removed by filtration.

The volatile materials and metal components are removed, and the organic impurities are oxidized and decomposed by the above processes. As a result, the content of iron and ash in the recovered terephthalic acid is largely reduced and the so-called thermal resistance which is considered as a barrier to ouer cone is largely enhanced.

A stoichiometric equivalent of ammonia gas relative to the recovered terephthalic acid is desirably used in the ammoniation process. At this time, oxidized inorganic metals are precipitated in the ammoniation process, and some decomposed organic impurities may coexist in the ammonium salt solution of the terephthalic acid. As colored materials, the coexisting impurities are removed through filtration and then adsorption processes, and purified diammonium terephthalate is thereby obtained.

After passing through these processes, demmoniation can be performed by heating to more than 200° C., or by neutralization with an acid such as sulfuric acid, in order to convert diammonium terephthalate into terephthalic acid. These processes are depicted in flow charts in FIG. 1 and FIG. 2, respectively.

Figure 2:
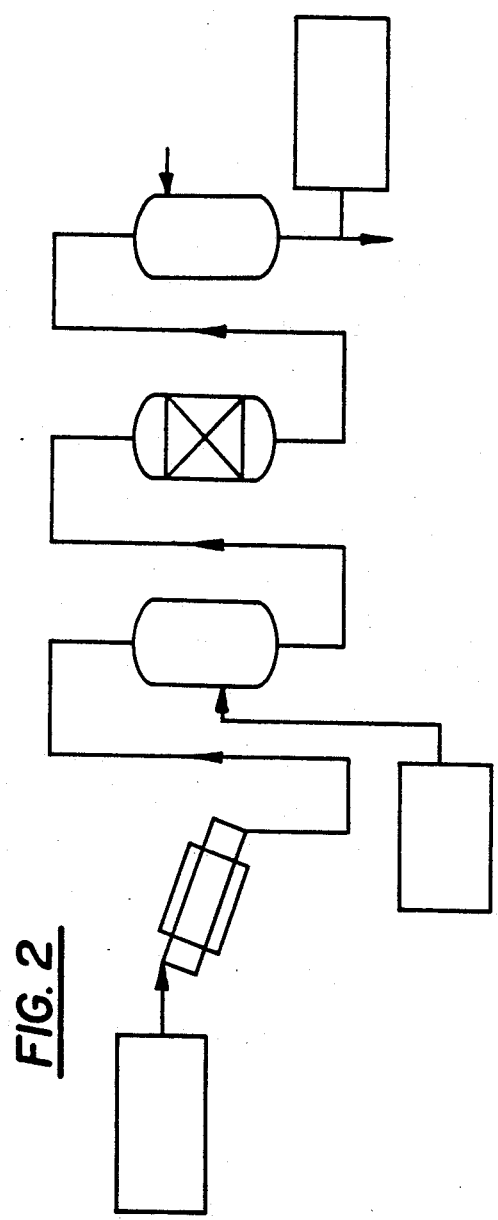
FIG. 2 is a flow sheet of a second embodiment of the process, in which diammonium terephthalate is deammoniated by neutralization with at least one acid, such as sulfuric acid.

In the flow charts of FIG. 1 and FIG. 2, impurity-containing crude terephthalic acid, which is recovered from alkali waste water by treating with acid, is crushed to 1–100 μm size, and passed through a thermal treatment process, i.e., treated for a specified time using a rotary kiln at 150°–300° C. and other treatment facilities under a stream of oxygen-containing gases.

In a thermal treatment process like this, a maximum amount of impurities is exposed, and terephthalic acid is converted into its diammonium salt by using ammoniation. At the same time, the inpurities coexist in the solution. To remove the coexisting impurities in the solution, it is necessary to pass the impurity-containing solution of diammonium salt through filtration and adsorption processes which use an adsorbent such as active carbon.

The highly purified terephthalic acid can be prepared from the diammonium salt solution after the filtration and absorption processes have been conducted, using deammoniation, either by thermal treatment in a rotary kiln or other treatment facilities under a stream of nitrogen gas according to the first embodiment of the process, depicted in FIG. 1, or by treating with acid according to the second embodiment of the process, depicted in FIG. 2.

Terephthalic acid which is prepared according to the above processes is as highly pure as polymer grade.

This invention is explained in more detail by the following examples, but the claims are not limited to these examples.

EXAMPLE 1

Impurity-containing terephthalic acid(500 g) was treated for 10 min with heat in the rotary kiln at 278°–282° C. under a stream of oxygen (0.2 l/min.), and converted into the solution of diammonium terephthalate using ammonia (113 g) and water (5.7 kg), and filtered using Whatman No. 41 filter paper under reduced pressure. Active charcoal (8.0 g) was added to the above filtrate. This charcoal-containing diammonium terephthalate solution was filtered, and the pH of the solution was controlled to 3.5 with sulfuric acid (170 ml).

The precipitated terephthalic acid was repeatedly suspended and filtered using deionized water (500 ml each) until the electric conductivity of the filtrate became 38.4 μmhos/cm, and the solid products were dried. Terephthalic acid purified in this way was analyzed by the following methods:

Acid number, Purity: titration method by potassium hydroxide

Ash content: weight analysis method which calculated the remaining quantity after heating 4 hrs at 450° C. and 2 hrs at 650° C.

Alkali transmittance: transmittance at 340 nm and 400 nm

Thermal resistance: thermal resistance at 340 nm and 400 nm after treating for 3 hrs at 280° C. in a muffle furnace.

Color(APHA): comparison with APHA standard solution.

Iron content: colorimetric method

4-CBA: analysis by polarographic method.

EXAMPLE 2

The same terephthalic acid (500 g) as used in Example 1 was treated for 10 min. with heat in a rotary kiln at 278°–282° C. under a stream of oxygen (0.2 l/min.), and converted into the diammonium salt using ammonia (113 g) and water (5.7 kg). The above solution was filtered, active charcoal (8 g) added thereto, and filtered again after stirring for 30 min. To convert the diammonium terephthalate to terephthalic acid, water was evaporated or the diammonium salt was crystallized at low temperature. After filtering and drying, the terephthalic acid is treated in a rotary kiln at 270°–290° C. for 60 min., yielding polymer grade terephthalic acid. Analytical methods were used as in Example 1.

EXAMPLE 3

The same terephthalic acid (500 g) as used in Example 1 was treated for 30 min. with heat in a rotary kiln at 248°–252° C. under a stream of oxygen gas (0.2 l/min.), and converted into the solution of diammonium terephthalate using ammonia (113 g) and water (5.7 kg). The resulting solution was filtered, active charcoal (8 g) added thereto, and filtered after stirring for 30 min. To the filtrate, sulfuric acid (170 ml) was added until the pH of the solution became 3.5, in order to convert the diammonium terephthalate into terephthalic acid. The precipitates were suspended and filtered repeatedly with deionized water (500 ml each) until the electrical conductivity of the filtrate became 38.0 μmhos/cm, and the solid cake was dried. The purified terephthalic acid according to the above process was analyzed by the same methods as were used in Example 1.

EXAMPLE 4

The same terephthalic acid (500 g) as used in Example 1 was treated for 30 min. with heat in a rotary kiln at 248°–252° C. under a stream of oxygen gas (0.2 l/min.), and converted to a solution of diammonium terephthalate using ammonia (113 g) and water (5.7 kg). The above solution was filtered, active charcoal (8 g) was added to the filtrate, and the solution filtered again after stirring for 30 min. To convert the diammonium terephthalate to terephthalic acid after filtration, water and remaining ammonia were completely removed at 100° C., and the purified terephthalic acid was prepared by treating for 60 min., with heat in the rotary kiln at 270°–290° C. Analytical methods were same as were used in Example 1.

The results of the above examples are presented in Table 2.

TABLE 2

| item | crude terephthalic acid | example 1 | example 2 | example 3 | example 4 |
| --- | --- | --- | --- | --- | --- |
| acid number (KOH mg/g) | 675 ± 2 | 673 | 675 | 674 | 673 |
| alkali transmittance | | | | | |
| 340 nm (%) | 87.8 | 90.2 | 95.4 | 95.0 | 94.0 |
| 400 nm (%) | 97.0 | 94.5 | 98.2 | 98.0 | 97.7 |
| thermal resistance | | | | | |
| 340 nm (%) | <1 | 84.7 | 90.2 | 79.4 | 90.5 |
| 400 nm (%) | <1 | 88.4 | 94.4 | 87.8 | 94.9 |
| color (APHA) | 20 | 10 | 10 | 10 | 10 |
| iron content (ppm) | 17 | 4.2 | 3.7 | 3.7 | 3.7 |
| 4-CBA (ppm) | <25 | <25 | <25 | <25 | <25 |
| ash content (ppm) | 150 | 10 | 10 | 10 | 10 |

In conclusion, according to this invention it is necessary to utilize the processes of thermal treatment, ammoniation, and adsorption techniques by adsorbents, in order to obtain polymer grade terephthalic acid from the crude terephthalic acid recovered by neutralization from alkali waste.

In addition, these processes are necessary to remove impurities efficiently, and to obtain polymer grade terephthalic acid. The terephthalic acid prepared according to the process of this invention is highly pure, pure enough to be used in polymerization reactions.

What we claim is:

1. A process for purifying a crude terephthalic acid obtained by neutralizing disodium terephthalate from alkali waste water from a polyester fabric weight-reduction process, comprising:
    (a) crushing said crude terephthalic acid to a particle size in the range of 0.1 to 1.500 μm;
    (b) thermally treating the crushed crude terephthalic acid particles in a kiln at 150° to 300° C. for oxidizing, decomposing and diffusing to outer surfaces of said particles;
    (c) combining the thermally treated particles with ammonia and water to produce an aqueous solution of diammonium terephthalate, containing impurities;
    (d) contacting said solution with an adsorbent, and filtering said solution for substantially removing said impurities therefrom; and
    (e) deammoniating said filtered solution and recovering terephthalic acid therefrom.

2. The process of claim 1, wherein:
    in step (e), said filtered solution is deammoniated by thermally treating said filtered solution, while contacting said filtered solution with a stream of nitrogen gas.

3. The process of claim 1, wherein:
    in step (e), said filtered solution is deammoniated by neutralization by an acid, thereby causing a precipitate of terephthalic acid to form; and separating said precipitate from the thereby depleted neutralized solution.

4. The process of claim 1, wherein:
    while step (b) is being conducted, the crushed crude terephthalic acid particles are contacted in said kiln by a stream of oxygen-containing gas, which has an oxygen content of 10 to 100 percent.

5. The process of claim 4, wherein:
    step (b) is conducted for a period of one minute to ten hours, and at an oxygen-containing gas flow rate of 0.01 to 1000 ml/minute.

* * * * *

UNITED STATES PATENT AND TRADEMARK OFFICE
CERTIFICATE OF CORRECTION

PATENT NO. : 5,210,292

DATED : May 11, 1993

INVENTOR(S) : PARK et al

It is certified that error appears in the above-identified patent and that said Letters Patent is hereby corrected as shown below:

On title page, change item

"[75] Inventors: Sang F. Park; Tae S. Chang; Young K. Lee, . . ."

to

--[75] Inventors: Sang E. Park; Tae S. Chang; Young K. Lee, . . . ---

Signed and Sealed this

Eighteenth Day of January, 1994

Attest:

BRUCE LEHMAN

Attesting Officer     Commissioner of Patents and Trademarks